United States Patent
Swanzey et al.

(10) Patent No.: US 11,013,408 B2
(45) Date of Patent: May 25, 2021

(54) CLINICAL DATA OBFUSCATION AND ENHANCEMENT SYSTEMS AND METHODS FOR WIRELESS MEDICAL DEVICES

(71) Applicant: Ascensia Diabetes Care Holdings AG, Basel (CH)

(72) Inventors: Todd T. Swanzey, Putnam Valley, NY (US); Gregory Stefkovic, Mahopac, NY (US); Christopher Dionisio, Millington, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 379 days.

(21) Appl. No.: 15/126,803

(22) PCT Filed: Mar. 18, 2015

(86) PCT No.: PCT/US2015/021313
§ 371 (c)(1),
(2) Date: Sep. 16, 2016

(87) PCT Pub. No.: WO2015/143071
PCT Pub. Date: Sep. 24, 2015

(65) Prior Publication Data
US 2017/0103176 A1    Apr. 13, 2017

Related U.S. Application Data

(60) Provisional application No. 61/955,472, filed on Mar. 19, 2014.

(51) Int. Cl.
*A61B 5/00*    (2006.01)
*G16H 10/65*    (2018.01)
(Continued)

(52) U.S. Cl.
CPC ........ *A61B 5/0002* (2013.01); *A61B 5/14532* (2013.01); *G06F 21/602* (2013.01);
(Continued)

(58) Field of Classification Search
CPC .............................. G16H 10/60; G16H 50/70
See application file for complete search history.

(56) References Cited

U.S. PATENT DOCUMENTS 5,724,428 A * 3/1998 Rivest ................... H04L 9/0625
380/28
6,708,272 B1 * 3/2004 McCown ................ H04L 9/083
380/278
(Continued)

FOREIGN PATENT DOCUMENTS

JP    H 07-170280    7/1995
JP    2006-6289081    10/2006
(Continued)

OTHER PUBLICATIONS

International Search Report, PCT/US2015/021313, dated Jul. 9, 2015 (3 pages).
(Continued)

*Primary Examiner* — John P Go
(74) *Attorney, Agent, or Firm* — Nixon Peabody LLP

(57) ABSTRACT

According to one aspect of the present invention, a sensor for diagnosing a physiological or physical state includes a measurement system configured to determine clinical data for one or more parameters related to the physiological or physical state, a first memory configured to store the clinical data, a transmitter configured to transmit the clinical data according to a first communications protocol, a receiver configured to receive enhanced data according to a second
(Continued)

communications protocol, and a second memory configured to store the enhanced data. The enhanced data is based on the clinical data.

18 Claims, 3 Drawing Sheets

(51) Int. Cl.
    *G16H 10/60*     (2018.01)
    *A61B 5/145*     (2006.01)
    *G16H 40/67*     (2018.01)
    *G06F 21/60*     (2013.01)
    *G06F 21/62*     (2013.01)

(52) U.S. Cl.
    CPC ......... *G06F 21/6254* (2013.01); *G16H 10/60* (2018.01); *G16H 10/65* (2018.01); *G16H 40/67* (2018.01); *A61B 2562/0295* (2013.01)

(56) References Cited

U.S. PATENT DOCUMENTS

| | | | |
|---|---|---|---|
| 7,716,467 | B1 | 5/2010 | Deffet |
| 7,889,069 | B2 | 2/2011 | Fifolt |
| 8,405,502 | B2 | 3/2013 | Teague |
| 2003/0154372 | A1* | 8/2003 | Barszcz .................. A61B 5/165 713/161 |
| 2004/0186746 | A1* | 9/2004 | Angst .................... G16H 10/60 705/3 |
| 2004/0236748 | A1* | 11/2004 | Coltrera ................. G06Q 50/24 |
| 2005/0192845 | A1* | 9/2005 | Brinsfield ........... G06F 19/3418 705/3 |
| 2005/0246185 | A1* | 11/2005 | Brown ................... G06Q 50/22 705/2 |
| 2006/0001551 | A1* | 1/2006 | Kraft .................. A61B 5/14532 340/870.16 |
| 2006/0173719 | A1* | 8/2006 | Kuhn ..................... G06Q 50/24 705/3 |
| 2009/0149722 | A1 | 6/2009 | Abolfathi |
| 2011/0081015 | A1 | 4/2011 | Parker |
| 2011/0208013 | A1* | 8/2011 | Phan ...................... A61B 5/002 600/301 |
| 2013/0067226 | A1* | 3/2013 | Kunde ................. H04L 9/0894 713/168 |

FOREIGN PATENT DOCUMENTS

| | | |
|---|---|---|
| JP | 2012-108745 | 6/2012 |
| JP | 2012-529926 | 11/2012 |
| JP | 2013-085895 | 5/2013 |
| JP | 2013-520284 | 6/2013 |
| WO | WO-2014088239 A1 * | 6/2014 ........... G06F 21/575 |

OTHER PUBLICATIONS

Written Opinion of the International Searching Authority, PCT/US2015/021313, dated Jul. 9, 2015 (7 pages).

* cited by examiner

CLINICAL DATA OBFUSCATION AND ENHANCEMENT SYSTEMS AND METHODS FOR WIRELESS MEDICAL DEVICES

CROSS-REFERENCE TO RELATED APPLICATIONS

This application is a U.S. national stage of International Application No. PCT/US2015/021313, titled "Clinical Data Obfuscation And Enhancement Systems And Methods For Wireless Medical Devices," and filed Mar. 18, 2015, which claims priority to and the benefits of U.S. Provisional Application No. 61/955,472, filed Mar. 19, 2014, the contents of which are hereby incorporated by reference herein in their entireties.

FIELD OF THE INVENTION

The present invention relates generally to medical devices and methods of using medical devices and, more particularly, to medical devices and methods for wireless communication of medical data between a sensor and a collector.

BACKGROUND OF THE INVENTION

Medical devices are increasingly incorporating wireless communication functionalities for a variety of reasons. In some instances, a first medical device is utilized for measuring clinical data, which is communicated to a second medical device for advanced analysis of the clinical data and/or archiving of the clinical data. For example, some blood glucose meters communicate test results to a personal computer for such purposes. As a result, the design of the blood glucose meter can be simplified to reduce the size or weight, to increase portability of the meter, to reduce the cost of manufacture, minimize computational resources, etc.

SUMMARY OF THE INVENTION

According to one aspect of the present invention, a sensor for diagnosing a physiological or physical state includes a measurement system configured to determine clinical data for one or more parameters related to the physiological or physical state, a first memory configured to store the clinical data, a transmitter configured to transmit the clinical data according to a first communications protocol, a receiver configured to receive enhanced data according to a second communications protocol, and a second memory configured to store the enhanced data. The enhanced data is based on the clinical data.

According to another aspect of the invention, a computer-implemented method of managing medical data includes determining, using a sensor, clinical data for the one or more parameters relating to a physiological state or a physical state of an individual, storing the clinical data in a first memory of the sensor, transmitting the clinical data from the sensor to a collector according to a first communications protocol, receiving enhanced data from a collector according to a second communications protocol, and storing the enhanced data in a second memory of the sensor. The enhanced data is based on the clinical data.

According to still another aspect of the invention, a sensor for diagnosing a physiological or physical state includes a measurement system configured to conduct a diagnostic analysis, a transmitter and a receiver configured to transmit and receive data, respectively, according to a plurality of different communications protocols, and computer-logic circuitry, including one or more controllers and one or more memory devices. The one or more memory devices store instructions that, when executed by the one or more controllers, cause the computer-logic circuitry to determine clinical data for one or more parameters related to the physiological or physical state, store the clinical data in a first memory area of the one or more memory devices, transmit the clinical data to a collector according to a first one of the plurality of communications protocols, receive enhanced data, based on the clinical data, from the collector according to a second one of the plurality of communications protocols, and store the enhanced data in a second memory area of the one or more memory devices.

According to yet another aspect of the invention, computer readable storage media is encoded with instructions for directing a sensor system to perform the above methods.

Additional aspects of the invention will be apparent to those of ordinary skill in the art in view of the detailed description of various embodiments, which is made with reference to the drawings, a brief description of which is provided below.

Figure 1:
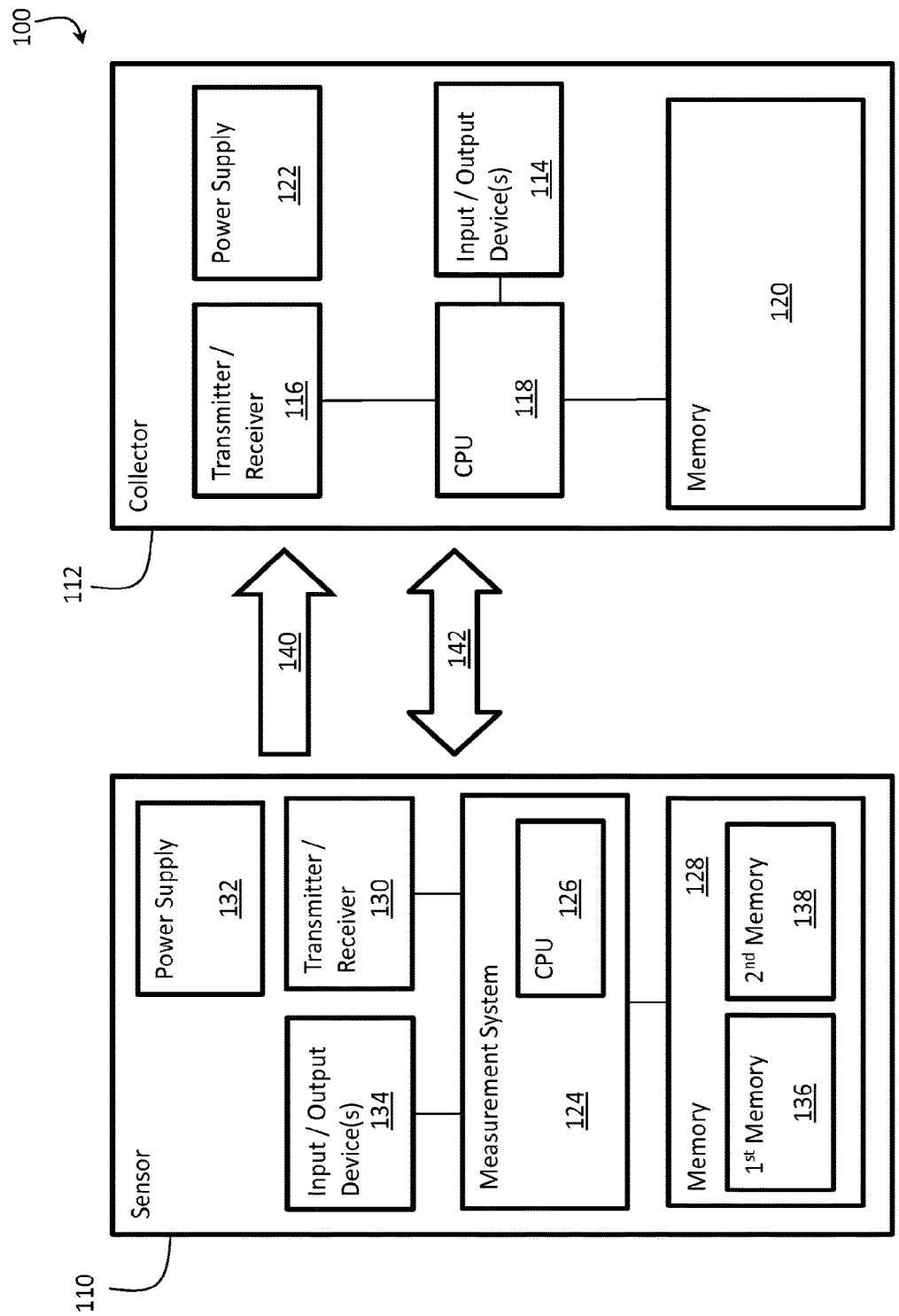
FIG. 1 is a schematic diagram of an exemplary medical data management system according to an embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

Existing medical device systems employing wireless communications have been found to suffer from a number of significant limitations. In particular, for example, existing medical device systems generally communicate according to industry standard communication protocols. Such standard communication protocols help harmonize the technical specifications of medical devices, improving industry efficiency, product compatibility, and end user experiences. While these standard communication protocols typically include some type of security features, often times such security features prove to be inadequate. Indeed, because the standard communication protocols are publicly available, the clinical data stored on the medical devices is prone to attack or collection by unauthorized persons. Another drawback of existing medical devices utilizing the standard communication protocols is that the data communications are required to be provided according to a particular formatting and, thus, are limited to only certain predefined fields of data.

According to aspects of the present disclosure, systems and methods are described for improving the storage, management, and wireless communication of medical data in a significantly more secure manner. This is accomplished while maintaining the ability of the medical devices to communicate via standard communications protocols so as to provide flexibility and ease of use in operating the medical devices.

Referring to FIG. 1, an exemplary schematic diagram of a medical-data-management system 100 is illustrated according to aspects of the present disclosure. The system 100 includes a sensor 110 and a collector 112. The sensor 110 and the collector 112 are distinct and separate devices configured to perform different functions for the diagnosis and/or treatment of an individual. The sensor 110 is a portable device configured to detect and measure clinical data for one or more parameters related to the physiological state and/or the physical state of an individual. As non-limiting examples, the sensor 110 can include biosensor devices (e.g., a blood glucose sensor, meter, and/or monitor), cardiac monitoring devices (e.g., a heart rate monitor or a Holter monitor), hemodynamic monitoring devices, respiratory monitoring devices, neurological monitoring devices, body temperature monitoring devices, childbirth monitoring devices, combinations thereof, and/or the like. According to some aspects of the present disclosure, the sensor 110 is a portable device that is sized to be easily carried, transported, and stored by an individual. According to additional and/or alternative aspects of the present disclosure, one or more components of the sensor 110 can be configured to be implanted within the body of an individual.

The collector 112 is configured to wirelessly receive and process the clinical data measured by the sensor 110. Non-limiting examples of the collector 112 include a desktop or laptop personal computer (PC), a handheld or pocket personal computer (HPC), a tablet computing device, a personal digital assistant (PDA), a mobile phone (e.g., a smartphone), combinations thereof, and/or the like. In some instances, the collector 112 may be a personal device owned and operated by the individual and, in other instances, the collector 112 may be owned and operated by the individual's healthcare provider.

The exemplary collector 112 illustrated in FIG. 1 includes a collector input/output device 114, a collector-communications-interface 116, a collector controller ("collector CPU") 118, a collector memory 120, and a collector-power-supply 122. The collector 112 is typically operated with the collector input/output devices 114, which may be external to, or integrated with, other components of the collector 112. For example, the collector input/output devices 114 can include one or more displays, audio speakers, touch screens, buttons, mice, joysticks, gesture-sensing devices, voice-recognition devices, combinations thereof and/or the like. The collector input/output devices 114 can be configured to receive user inputs and transform the user inputs to electronic data signals indicative of the user inputs, which are received by the collector CPU 118 for processing.

The collector communications-interface 116 is configured to facilitate data communications between the sensor 110 and the collector 112, as described in greater detail below. The collector-power-supply 122 can include any source of electrical power that can be delivered to the collector 112. While the collector-power-supply 122 is illustrated as being incorporated into the collector 112 (e.g., a battery), it should be understood that the collector-power-supply 122 can be external to the collector 112 (e.g., the electrical grid).

In general, the collector CPU 118 is capable of receiving and executing any number of programmed instructions. In particular, the collector CPU 118 is configured to process the clinical data received from the sensor 110, as described in greater detail below. The collector memory 120 is configured to store the clinical data received from the sensor 110 and/or data resulting from the processing of the clinical data. The collector memory 120 can further store instructions for performing the operations of the collector 112 described herein. As non-limiting examples, the collector memory 120 can include read only memory (ROM), random access memory (RAM), magnetic disk storage media, optical storage media, flash memory, combinations thereof, and/or the like.

The exemplary sensor 110 shown in FIG. 1 includes a measurement system 124, a sensor controller ("sensor CPU") 126, a sensor memory 128, a sensor-communications-interface 130, a sensor-power-supply 132, and a sensor input/output device 134. The measurement system 124 is configured to measure and determine the clinical data for the parameter(s) related to the physiological and/or the physical state of the individual. For example, the measurement system 124 can include one or more electrical sensors, optical sensors, mechanical sensors, chemical sensors, and/or combinations thereof (e.g., electromechanical sensors, electrochemical sensors, etc.) communicatively coupled to the sensor CPU 126 to determine the clinical data for the parameter(s) related to the physiological and/or physical state of the individual. As non-limiting examples, the measurement system 124 can include one or more electrodes, image sensors, pressure sensors, accelerometers, fluid and/or gas flow sensors, temperature sensors, superconducting quantum interference devices (SQUID), ion specific field effect transistors (ISFET), negative temperature coefficient (NTC) resistors, positive temperature coefficient (PTC) resistors, band gap detectors, ion membranes, enzyme reactors, combinations thereof, and/or the like.

The sensor CPU 126 is further communicatively coupled to the sensor memory 128. The sensor memory 128 can be a machine-readable storage media including any mechanism that stores information and provides the information in a form readable by a machine. For example, the sensor memory 128 can include read only memory (ROM), random access memory (RAM), magnetic disk storage media, optical storage media, flash memory, combinations thereof, and/or the like. The sensor memory 128 can store instructions for performing the operations of the sensor 110 described herein.

The sensor memory 128 includes at least two separate and distinct memory areas. A first memory area 136 is configured to store only the clinical data determined by the measurement system 124. A second memory area 138 is configured to store only enhanced data received from the collector 112, as will be described in greater detail below. It should be understood that the first memory area 136 and the second memory area 138 can be provided by a single memory device or a plurality of separate and distinct memory devices.

The sensor CPU 126 is also communicatively coupled to the sensor-communications-interface 130, which facilitates data communications between the sensor 110 and the collector 112. In particular, the sensor-communications-interface 130 and the collector-communications-interface 116 employ compatible technologies that facilitate the exchange of data between the sensor 110 and the collector 112 according to at least two different communications protocols. As is known to those of ordinary skill in the art, a communications protocol is a set of rules for data exchange (e.g., defining the syntax, semantics, and synchronization of the data exchange). Thus, the at least two communications protocols can differ from each other in at least one of the syntax (e.g., data format), the semantics, and/or the synchronization utilized to exchange data between the sensor 110 and the collector 112.

According to some aspects of the present disclosure, the sensor-communications-interface 130 and the collector-communications-interface 116 can be configured to communicate via radio-frequency (RF) communications (e.g., a short-range RF telemetry), such as Bluetooth® wireless technologies, Zigbee, Z-Sense™ technology, FitSense, BodyLAN™ system, other RF technologies, etc. According to additional and/or alternative aspects, the sensor-communications-interface 130 and the collector-communications-interface 116 can be configured to communicate via other wireless technologies such as, for example, infrared (IR) technologies or other optical technologies. It should be understood that the sensor-communications-interface 130 and the collector-communications-interface 116 can include a transmitter for transmitting data and/or a receiver for receiving data according to the communications protocols employed. According to some aspects, a common transmitter/receiver can be provided for communicating according to both of the at least two communications protocols. According to alternative aspects, a different transmitter/receiver can be provided for each of the at least two communications protocols in the sensor-communications-interface 130 and the collector-communications-interface 116. Alternatively a wired interface such as a USB connection may be established between the transmitter of the sensor-communications-interface 130 and the receiver of the collector-communications-interface 116 for transmitting and receiving data.

The sensor-power-supply 132 can include any source of electrical power that can be delivered to the sensor 110. While the sensor-power-supply 132 is illustrated as being incorporated into the sensor 110 (e.g., a battery), it should be understood that the sensor-power-supply 132 can be external to the sensor 110 (e.g., the electrical grid).

The sensor 110 can further include one or more sensor input/output devices 134 to facilitate operation of the sensor 110 by the individual user and/or to communicate information to the user. For example, the sensor input/output devices 134 can include one or more displays, audio speakers, touch screens, buttons, mice, joysticks, gesture-sensing devices, voice-recognition devices, combinations thereof and/or the like. The sensor input/output devices 134 can be configured to receive user input(s) and transform the user input(s) to electronic data signals indicative of the user input(s), which are received by the sensor CPU 126 for processing.

Figure 2:
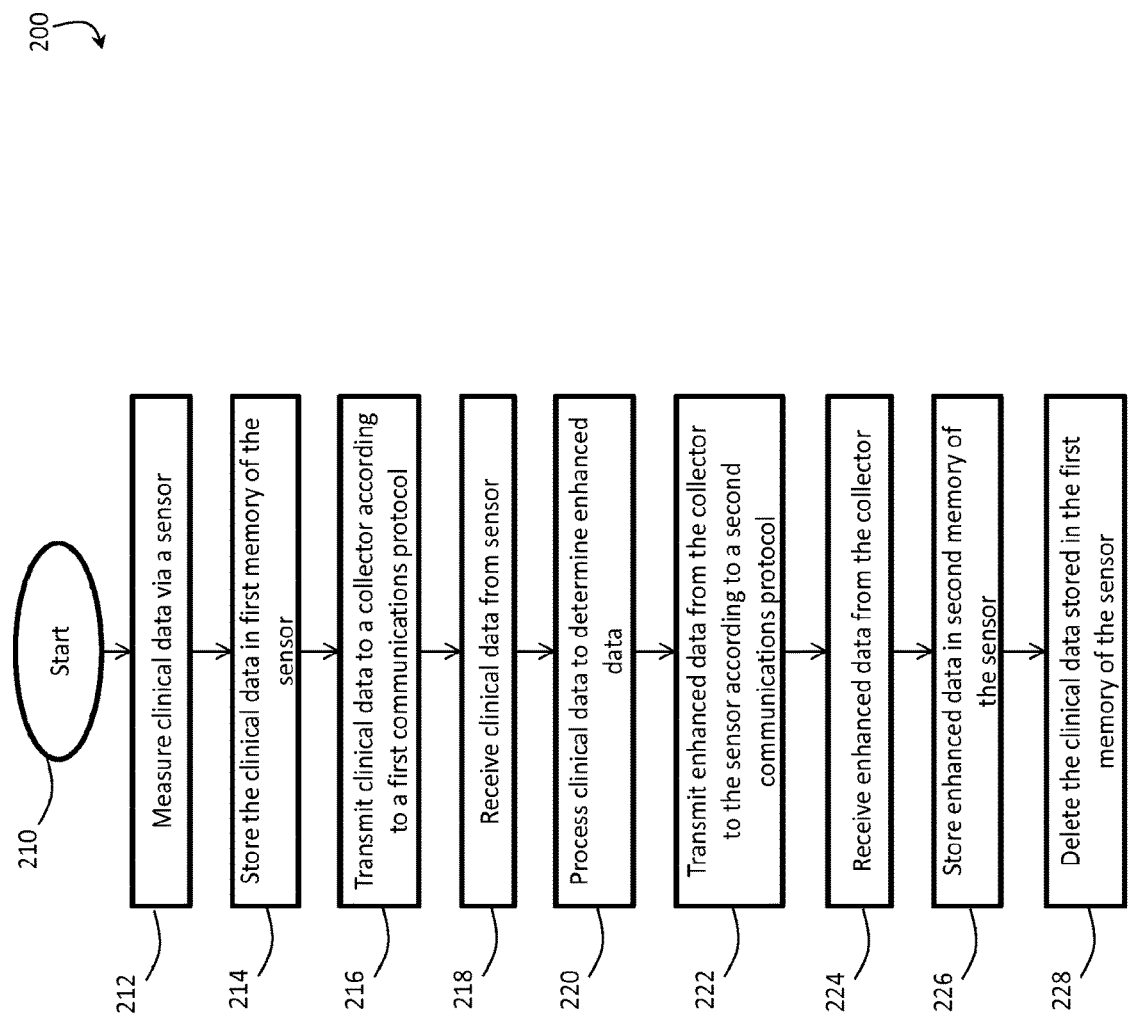
FIG. 2 is a flowchart of an exemplary method for managing medical data, according to an embodiment of the present invention.

Referring now to FIG. 2, an exemplary flowchart of a process 200 for managing medical data wirelessly communicated between a sensor 110 and a collector 112 is illustrated according to aspects of the present disclosure. At step 210, the process is initiated. At step 212, the clinical data for the parameter(s) related to a physiological and/or a physical state of an individual is measured and determined by a sensor 110. At step 214, the clinical data is stored in the first memory 136 of the sensor 110.

At step 216, the clinical data is transmitted from the sensor 110 to a collector 112 according to a first communications protocol 140. The first communications protocol 140 can be a publicly available communications protocol or an industry standard communications protocol, such as those provided by the International Organization for Standardization (ISO), the International Telecommunications Union (ITU), or the Institute of Electrical and Electronics Engineers (IEEE). Additionally, a number of Bluetooth Core Specifications and associated Profiles and Services have been issued for medical-device-specific communications protocols, which have been adopted by various medical device industries. As one non-limiting example, the Bluetooth Profile Specification titled "GLP" and the Glucose Service Specification titled "GLS" have been adopted for data exchanges between a blood glucose sensor 110 and a collector 112. These Bluetooth Profile and Service Specifications are currently available at www.bluetooth.org/en-us/specification/adopted-specifications. Because the clinical data is communicated from the sensor 110 to the collector 112 according to an industry standard communications protocol, the sensor 110 may be compatible with various different collectors 112. According to aspects of the present disclosure, the clinical data is not encrypted when stored in the first memory 136 of the sensor 110 or during transmission according to the first communications protocol 140. It is contemplated that, according to some aspects, the first communications protocol 140 can be configured for only one-way communication of stored data (i.e., from the sensor 110 to the collector 112).

At step 218, the clinical data is received by the collector 112 according to the first communications protocol 140. At step 220, the clinical data is processed by the collector 112 to determine the enhanced data based on the clinical data. Generally, the collector 112 can include advanced processing features that may not be included for the sensor 110 and with which the enhanced data can be determined based on the clinical data. According to some aspects of the present disclosure, the clinical data is processed to enhance the security of the clinical data. For example, the processing can include encrypting and/or hashing the clinical data to determine the enhanced data.

According to additional and/or alternative aspects of the present disclosure, the enhanced data can include one or more additional data fields containing additional information based on or associated with the clinical data. For example, the enhanced data can include data fields for information relating to time stamp data for tests results, statistical analysis data, summary analysis data providing feedback on test results, analysis of the clinical data relative to user-specific target ranges, predictive analysis data, recommended medication dosages based on analysis of the clinical data, combinations thereof, and/or the like. More generally, the clinical data can include a first set of one or more data fields and the enhanced data can include a second set of one or more data fields that are different from the first set. In other words, according to some aspects, the enhanced data need not necessarily have more data fields than the clinical data according to some aspects—just different data fields.

At step 222, the enhanced data is transmitted from the collector 112 to the sensor 110 according to a second communications protocol 142. At step 224, the enhanced data is received by the sensor 110 from the collector 112. At step 226, the enhanced data is stored in the second memory 138 of the sensor 110. Accordingly, the system 100 of the present disclosure advantageously allows for bi-directional communications of data related to the clinical data in contrast to existing medical devices employing only industry standard communications protocols, which typically permit the collector 112 to only read data from the sensor 110 (i.e., one-way communication of clinical data).

According to some aspects in which the enhanced data is encrypted, only the collector 112 can decrypt the enhanced data. That is, the sensor 110 does not include any decryption capabilities (e.g., a decryption key), further mitigating the risk that an unauthorized attempt to access the enhanced data on the sensor 110 will be successful. As a result, however, the sensor 110 cannot utilize the enhanced data itself. Rather, the sensor 110 acts as a secure portable medical records device. In some instances, only the user and/or the user's designated healthcare provider may have access to the appropriate decryption key required to access to the user's enhanced data on the sensor 110. In other instances, a decryption key can be made available to emergency medical technicians (EMTs), doctors, other healthcare providers, or the like. This may be particularly beneficial in emergency situations. For example, if an individual suffers a diabetic seizure while traveling away from home, an EMT may be able to better treat the individual by quickly accessing the individual's glucose concentration test result history stored on the sensor 110 carried by the individual.

According to some aspects in which the enhanced data includes one or more additional data fields, the sensor 110 also may not be able to utilize some or all of the enhanced data due to the sensor 110 omitting the advanced processing functions of the collector 112. According to additional and/or alternative aspects, the sensor 110 also may not be able to utilize the enhanced data due to formatting differences between the enhanced data and the clinical data. In either of such instances, the sensor 110 can also function as a secure portable medical records device as described above.

According to some aspects of the present disclosure, the sensor 110 can be configured such that the second memory 138 can only be wirelessly accessed by another device (e.g., the collector 112) in response to the sensor-communications-interface 130 receiving data communications according to the second communications protocol 142. In this way, the enhanced data stored on the second memory 138 can be further secured against unauthorized attempts to access it. This may provide a particularly effective layer of security where the second communications protocol 142 is not publicly available, not widely adopted, or not an industry standard communications protocol (e.g., a custom communications protocol).

According to some aspects of the present disclosure, at step 228, the clinical data stored in the first memory 136 of the sensor 110 can be deleted as the more secure enhanced data stored in the second memory 138 contains the necessary information needed for medical record purposes. Thus, by deleting the unencrypted clinical data, which can be accessed via the publicly available first communications protocol 140 configured for compatibility with a vast number of devices, the system 100 can minimize or, in some instances, eliminate the risk that the user's medical information is obtained by an unauthorized person. According to some aspects, the deletion of the clinical data from the first memory 136 can be triggered in response to the enhanced data being successfully stored in the second memory 138. According to additional and/or alternative aspects, the deletion of the clinical data from the first memory 136 can be triggered in response to a user input received via the sensor input/output device 134. It is contemplated that, in some embodiments, the sensor 110 can be configured to automatically prompt the user via the sensor input/output device 134 to request such a user input in response to the enhanced data being successfully stored in the second memory 138.

As described above, once stored in the second memory 138 of the sensor 110, the enhanced data can subsequently be accessed by the collector 112 via wireless data communications according to the second communications protocol 142. In this way, the sensor 110 can be advantageously utilized as a secure portable medical records device. Thus, the second communications protocol 142 is configured to permit bi-directional data communications between the sensor 110 and the collector 112.

FIG. 2, described by way of example above, represents one algorithm that corresponds to at least some instructions executed by the sensor CPU 126 and/or the collector CPU 118 in FIG. 1 to perform the above described functions associated with the described concepts. It is also within the scope and spirit of the present concepts to omit steps, include additional steps, and/or modify the order of steps presented above. For example, the process 200 can further include additional step(s) to store the clinical data and/or the enhanced data in the collector memory 120.

The systems and methods of the present disclosure are particularly advantageous to individuals who are actively involved in monitoring and recording measurements of health related data. For example, the systems and methods of the present disclosure can be particularly advantageous to individuals who actively monitor and record measurements related to blood glucose concentrations and/or other analytes of interest in a person's blood or other fluid.

Figure 3:
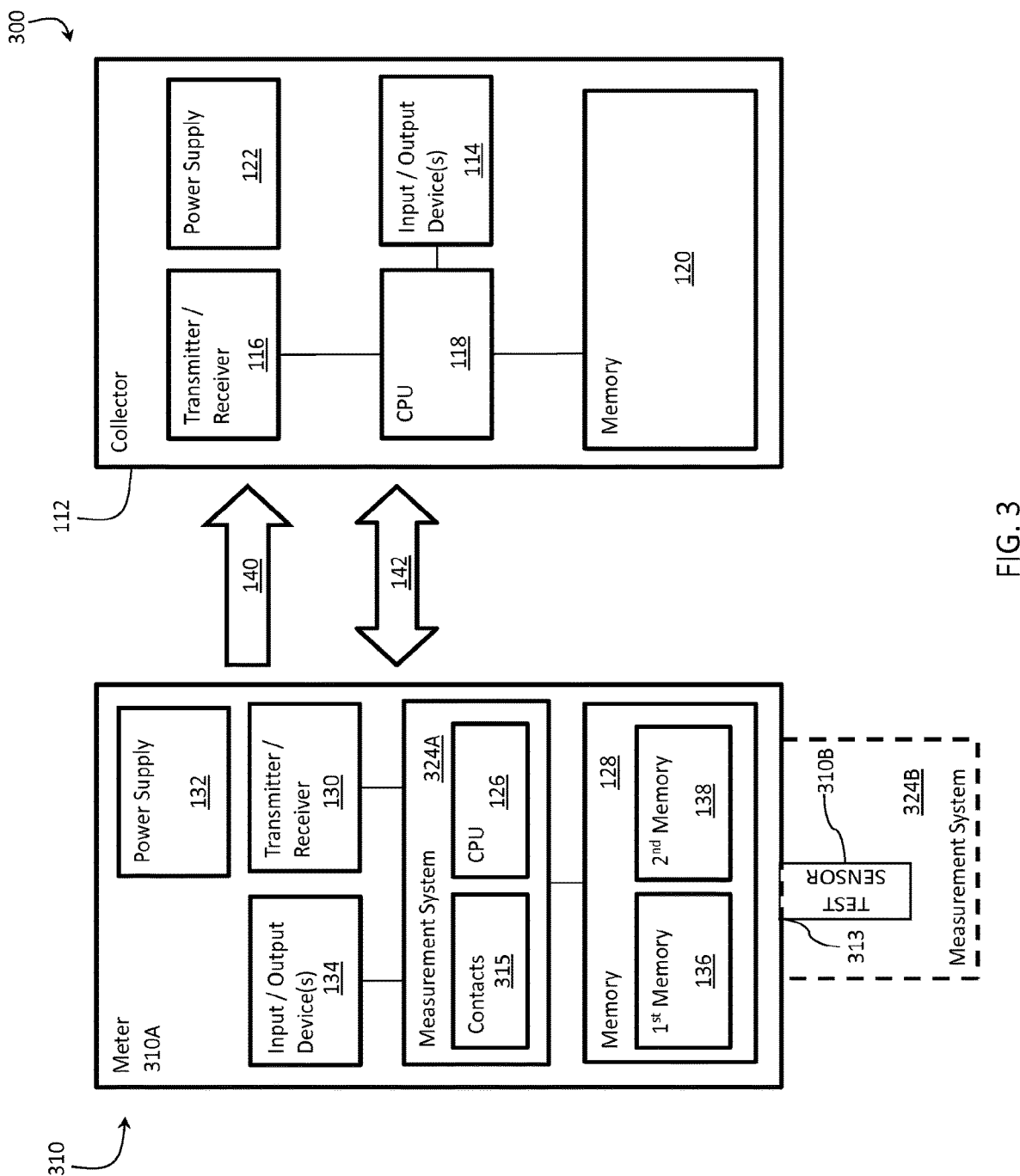
FIG. 3 is a schematic diagram of an exemplary medical data management system including a glucose meter according to an embodiment of the present invention.

FIG. 3 illustrates an exemplary sensor 310 including a meter 310A and a test sensor 310B for communicating with the collector 112 described above. The sensor 310 includes the sensor controller ("sensor CPU") 126, the sensor memory 128, the sensor-communications-interface 130, the sensor-power-supply 132, and the sensor input/output device 134 as described above. Additionally, the sensor 310 includes a measurement system 324 that is defined by components of the meter 324A and components of the test sensor 324B.

The meter 310A includes a port 313 for receiving and analyzing a fluid sample on the test sensor 310B. The test sensor 310B is configured to receive a fluid sample that is analyzed using the meter 310A. Analytes that may be analyzed include glucose, lipid profiles (e.g., cholesterol, triglycerides, LDL and HDL), microalbumin, hemoglobin $A_1C$, fructose, lactate, or bilirubin. Analyte information may, such as analyte concentrations, may be determined. The analytes may be in a whole blood sample, a blood serum sample, a blood plasma sample, other body fluids like ISF (interstitial fluid) and urine, and non-body fluids.

The test sensor 310B includes a fluid-receiving area (not shown) for receiving a fluid sample. A user may employ a lancet or a lancing device to pierce a finger or other area of the body to produce a fluid sample at the skin surface. The user may then collect this sample (e.g., blood sample) by placing the test sensor 310B into contact with the sample. The fluid-receiving area may contain a reagent that reacts with the sample to indicate the information related to an analyte in the sample, such as analyte concentration.

The test sensor 310B may be an electrochemical test sensor. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable. The reagent typically contains an enzyme, such as glucose oxidase, which reacts with the analyte and with an electron acceptor such as a ferricyanide salt to produce an electrochemically measurable species that can be detected by the electrodes. Other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte.

Alternatively, the test sensor 310B may be an optical test sensor. Optical test sensor systems may use techniques such as transmission spectroscopy, absorption spectroscopy, diffuse reflectance, fluorescence spectroscopy, fluorescence resonance energy transfer, combinations thereof, and others for measuring the analyte concentration. An indicator reagent system and an analyte in a sample of body fluid react to alter light that is directed to the test sensor 310B. The degree of light alteration is indicative of the analyte concentration in the body fluid.

Some commercially available test sensors that may be used include those that are available commercially from Bayer HealthCare LLC (Whippany, N.J.). These test sensors include, but are not limited to, those used in the Ascensia® CONTOUR® blood glucose monitoring system, the Ascensia® BREEZE® and BREEZE®2 blood glucose monitoring system, and the Ascensia® Elite® and Elite® XL blood glucose monitoring system. Other test sensors, in addition to the ones listed above, may be incorporated into the methods and systems of the present invention.

In FIG. 3, the meter 310A receives and engages the test sensor 310B. The meter 310A measures the concentration of analyte for the sample collected by the test sensor 310B. The meter 310A may include contacts 315 for the electrodes to detect the electrochemical reaction of an electrochemical test sensor. Alternatively, the meter 310A may include an optical detector (not shown) to detect the degree of light alteration for an optical test sensor. To calculate the actual concentration of analyte from the electrochemical or optical reaction measured by the meter 310A and to generally control the procedure for testing the sample, the meter 310A employs the sensor CPU 126, which may execute programmed instructions according to a measurement algorithm. Data processed by the sensor CPU 126 may be stored in the sensor memory 128. Furthermore, the meter 310A may include the sensor input/output devices 134, which includes a display (e.g., a liquid-crystal display or the like). Pushbuttons, a scroll wheel, touch screens, or a combination thereof, may also be provided as a part of the sensor input/output devices 134 to allow a user to interact with the meter 310A. The display typically shows information regarding the test results, the testing procedure and/or information in response to signals input by the user.

As described above, although the system 300 is configured to measure an analyte concentration in a fluid sample, the systems 100 and methods 200 are not limited to receiving and managing information from the testing of an analyte, such as blood glucose. Indeed, the systems 100 and methods 200 of the present disclosure can receive data from other systems or devices that measure and/or record health data and do not require analyte testing, such as body-temperature measurements, blood-pressure measurements, heart rate measurements, blood-oxygen content measurements, breathing measurements for chronic obstructive pulmonary disease (COPD) analysis, weight measurements for analyzing Lasix use, or the like.

As described above, the present disclosure includes systems having controllers (i.e., the sensor CPU 126 and the collector CPU 118) for providing various functionality to process information and determine results based on inputs. Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device that executes software, or stored instructions. In general, physical processors and/or machines employed by embodiments of the present disclosure for any processing or evaluation may include one or more microprocessors, field programmable gate arrays (FPGA's), digital signal processors (DSP's), micro-controllers, and the like, programmed according to the teachings of the exemplary embodiments of the present disclosure, as is appreciated by those skilled in the computer and software arts. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media (e.g., the sensor memory 128 and/or the collector memory 120), the exemplary embodiments of the present disclosure may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the exemplary embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A sensor for diagnosing a physiological or physical state, comprising:
   a measurement system configured to determine clinical data for one or more parameters related to the physiological or physical state of a patient;
   a first memory configured to store the clinical data, wherein the clinical data includes a first set of one or more data fields;
   a transmitter configured to transmit the clinical data to a collector according to a first communications protocol, wherein the collector includes advanced processing functions to determine enhanced data based on processing the clinical data determined by the measurement system;
   a receiver configured to receive the enhanced data according to a second communications protocol having a set of rules for data exchange that are not publicly available, the enhanced data including different information from the clinical data and wherein the enhanced data includes the first set of one or more data fields and one or more additional data fields, including a recommended medication dosage based on the clinical data, wherein the advanced processing functionality of the collector is omitted from the measurement system, and wherein the measurement system is not able to utilize the enhanced data; and
   a second memory configured to store only the enhanced data.

2. The sensor of claim 1, wherein the clinical data is stored in the first memory and transmitted by the transmitter in an unencrypted state.

3. The sensor of claim 2, wherein the enhanced data is in an encrypted state when received by the receiver and stored in the second memory.

4. The sensor of claim 3, wherein the enhanced data includes hashing.

5. The sensor of claim 1, further comprising a controller configured to operatively control the measurement system, the transmitter, and the receiver, the controller being further configured to delete the clinical data from the first memory in response to the receiver receiving the enhanced data based on the clinical data.

6. The sensor of claim 1, wherein the one or more additional data fields includes data relating to at least one of a statistical analysis or a predictive trend.

7. The sensor of claim 1, wherein the clinical data includes a measured blood glucose concentration.

8. A method of managing medical data, comprising:
   determining, using a sensor, clinical data for the one or more parameters relating to a physiological state or a physical state of an individual;
   storing the clinical data in a first memory of the sensor, wherein the clinical data includes a first set of one or more data fields;
   transmitting the clinical data from the sensor to a collector according to a first communications protocol, wherein the collector includes advanced processing functions;
   determining enhanced data based on the collector processing the clinical data determined by the measurement system;
   receiving the enhanced data from the collector according to a second communications protocol having a set of rules for data exchange that are not publicly available, the enhanced data including different information from the clinical data and wherein the enhanced data includes the first set of one or more data fields and one or more additional data fields, including a recommended medication dosage based on the clinical data, wherein the advanced processing functionality of the collector is omitted from the measurement system, and wherein the measurement system is not able to utilize the enhanced data; and
   storing only the enhanced data in a second memory of the sensor.

9. The method of claim 8, further comprising deleting the clinical data in the first memory after the enhanced data is received.

10. The method of claim 8, wherein the enhanced data is in an encrypted state when received by the sensor.

11. The method of claim 8, wherein the first communications protocol is a publicly available industry standard communications protocol and the second communications protocol is a non-publicly available custom communications protocol.

12. The method of claim 8, further comprising:
    receiving the clinical data at the collector according to the first communications protocol;
    processing the clinical data, using the collector, to determine the enhanced data; and
    transmitting the enhanced data from the collector to the sensor.

13. The method of claim 12, wherein the collector comprises a personal computer, a tablet computer, or a mobile phone.

14. The method of claim 13, wherein the sensor is a biosensor configured to determine a concentration of an analyte in a fluid sample.

15. The method of claim 8, further comprising transmitting the enhanced data from the sensor to the collector according to the second communications protocol.

16. A sensor for diagnosing a physiological or physical state, comprising:
    a measurement system configured to conduct a diagnostic analysis of a patient;
    a transmitter and a receiver configured to transmit and receive data, respectively, according to a plurality of different communications protocols; and
    computer-logic circuitry, including one or more controllers and one or more memory devices, the one or more memory devices storing instructions that, when executed by the one or controllers, cause the computer-logic circuitry to:
      determine clinical data for one or more parameters related to the physiological or physical state of the patient from the measurement system;
      store the clinical data in a first memory area of the one or more memory devices wherein the clinical data includes a first set of one or more data fields;
      transmit the clinical data to a collector according to a first one of the plurality of communications protocols, wherein the collector includes advanced processing functions to determine enhanced data based on processing the clinical data determined by the measurement system;

receive the enhanced data, based on the clinical data, from the collector according to a second one of the plurality of communications protocols having a set of rules for data exchange that are not publicly available, wherein the enhanced data includes information different from the clinical data and wherein the enhanced data includes the first set of one or more data fields and one or more additional data fields, including a recommended medication dosage based on the clinical data, and wherein the advanced processing functionality of the collector is omitted from the measurement system, and wherein the measurement system is not able to utilize the enhanced data; and store only the enhanced data in a second memory area of the one or more memory devices.

17. The sensor of claim 16, wherein the instructions further cause the computer-logic circuitry to delete the clinical data from the first memory area.

18. The sensor of claim 16, wherein the clinical data is unencrypted and the enhanced data is encrypted.

* * * * *